US008862634B2

(12) United States Patent
Fuladinashta et al.

(10) Patent No.: US 8,862,634 B2
(45) Date of Patent: Oct. 14, 2014

(54) APPARATUS, METHOD AND COMPUTER-READABLE STORAGE MEDIUM FOR ASSIGNING PATIENT STUDIES FOR PEER REVIEW

(75) Inventors: Fari Fuladinashta, Richmond (CA); Bo Liang, Surrey (CA); Hong Chen, Burnaby (CA); Denis Ng, Vancouver (CA); Christine Callaghan, Vancouver (CA); Ethel Zammit, Vancouver (CA); Brian Ding, Surrey (CA); Ka Kiu Chow, Vancouver (CA)

(73) Assignee: McKesson Financial Holdings, Hamilton (BM)

( * ) Notice: Subject to any disclaimer, the term of this patent is extended or adjusted under 35 U.S.C. 154(b) by 448 days.

(21) Appl. No.: 13/075,851

(22) Filed: Mar. 30, 2011

(65) Prior Publication Data

US 2012/0254206 A1 Oct. 4, 2012

(51) Int. Cl.
*G06F 17/30* (2006.01)
*G06F 19/00* (2011.01)

(52) U.S. Cl.
CPC ............ *G06F 19/321* (2013.01); *G06F 19/327* (2013.01)
USPC ........... 707/804; 707/706; 707/721; 707/732; 707/795; 707/767

(58) Field of Classification Search
USPC ......... 707/706, 721, 732, 737, 767, 741, 795, 707/804
See application file for complete search history.

(56) References Cited

U.S. PATENT DOCUMENTS

2005/0114140 A1 * 5/2005 Brackett et al. ............... 704/270
2010/0138241 A1 * 6/2010 Ruark et al. ...................... 705/3

* cited by examiner

*Primary Examiner* — Sana Al Hashemi
(74) *Attorney, Agent, or Firm* — Alston & Bird LLP

(57) ABSTRACT

An apparatus is provided that includes a processor and a memory storing executable instructions that in response to execution by the processor cause the apparatus to perform a number of functions, including identification of a target number that indicates a number of reported image studies for peer review. The apparatus is caused to identify users having user characteristics that match properties of the reported image studies. The user characteristics include a specialty (modality specialty and body-region specialty) that matches the reported image studies, or an associated medical facility that matches an associated medical facility of the reported image studies. The apparatus is caused to assign the target number of reported image studies to the identified users. The apparatus may be further caused to identify users that have previously performed a user-initiated peer review of a reported image study, and reduce their assigned image studies accordingly.

18 Claims, 2 Drawing Sheets

START

40 IDENTIFY TARGET NUMBER

42 IDENTIFY USERS SUCH AS THOSE HAVING MATCHING MODALITY, BODY-REGION SPECIALTIES, ASSOCIATED MEDICAL FACILITY OR THE LIKE

44 REDUCE TARGET NUMBER BY NUMBER OF "ON-THE-FLY" REVIEWS BY IDENTIFIED USERS

46 ASSIGN REDUCED NUMBER OF REPORTED STUDIES TO USERS

STOP

APPARATUS, METHOD AND COMPUTER-READABLE STORAGE MEDIUM FOR ASSIGNING PATIENT STUDIES FOR PEER REVIEW

FIELD OF THE INVENTION

The present invention generally relates to medical studies of patients, and more particularly, to assigning patient studies for peer review.

BACKGROUND OF THE INVENTION

Medical imaging often includes creating images of regions of the human body for clinical purposes such as examination, diagnosis and/or treatment. These images may be acquired by a number of different imaging modalities including, for example, ultrasound (US), magnetic resonance (MR), positron emission tomography (PET), computed tomography (CT), mammograms (MG) digital radiology (DR), computed radiology (CR) or the like. In a number of example medical imaging workflows, such as in the case of a picture archiving and communication system (PACS), an image study for a patient may include one or more acquired images of the patient along with information that may reside with or otherwise accompany the images. This information may include, for example, a study identifer as well as patient information such as the patient's name, demographics, medical record number or the like. The information may also include, for example, an indication of the modality that acquired the images of the study, the body region depicted in the images and/or the medical facility where the modality acquired the images.

Once a patient study has been created, the study may be stored in a database of a central storage device. At this stage, the study may be considered an unreported study. At some point after its creation, the study may be retrieved by a workstation where the study may be reviewed by a medical professional such as a radiologist who may make one or more diagnoses or other assessments of the patient from the study, and record those diagnoses or other assessments in a text-based report. This report may then be stored in an information system such as a hospital information system (HIS), radiology information system (RIS) or the like, where the report may be linked or otherwise associated with the image study such as by study identifier, patient name, medical record number or the like. At this stage, the study may be considered a reported study.

A more recent effort has been made in the medical community to improve the quality of medical care, and as part of this effort, a focus has been placed on performance of medical professionals. Peer review is one example technique that has been developed to evaluate performance, and that has been instituted as a requirement by a number of medical agencies including the American College of Radiology (ACR). In one example of a peer review process, after being reported, the patient study including its report of diagnoses/assessments may then be subject to review by one or more other medical professionals who evaluate the accuracy of the diagnoses/assessments.

SUMMARY OF THE INVENTION

In light of the foregoing background, exemplary embodiments of the present invention provide an apparatus, method and computer-readable storage medium for assigning for peer review reported image studies including image studies and reports. According to one aspect of exemplary embodiments of the present invention, an apparatus is provided that includes a processor and a memory storing executable instructions that in response to execution by the processor cause the apparatus to at least perform a number of functions. The apparatus is caused to identify a target number that indicates a number of reported image studies for peer review, where each reported image study is an image study having an associated report. The apparatus is caused to identify a plurality of users having user characteristics that match properties of the reported image studies. The user characteristics include a specialty that matches the reported image studies, or associated medical facility that matches an associated medical facility of the reported image studies. The aforementioned specialty includes a modality specialty that matches a modality of the reported image studies, and a body-region specialty that matches a body region of which the reported image studies include at least one image. And the apparatus is caused to assign the target number of reported image studies from a plurality of available reported image studies to the plurality of users. For example, the target number of reported image studies may be randomly or pseudo-randomly selected from the plurality of available reported image studies.

In one example, at least a portion of the identified users may have previously performed a user-initiated peer review of a first number of reported image studies. In this example, the apparatus may be further caused to reduce the target number by the first number. The apparatus may then be caused to assign the reduced target number of reported image studies, where each user may be assigned an equal portion of the target number of reported image studies less any of the first number of reported image studies of which the user has previously performed user-initiated peer review. In one example, the apparatus may be caused to identify a target number $n \geq 2$ and $m \geq 2$ users, where the users have previously performed user-initiated peer review of $r \geq 1$ reported image studies. In this example, the apparatus may be caused to assign $(n-r)$ reported image studies, with each user being assigned $n/m$ reported image studies less any of the $r$ reported image studies of which the user has previously performed user-initiated peer review.

In a more particular example, the plurality of users may include at least a first user having previously performed user-initiated peer review of $x \geq 0$ reported image studies, and a second user having previously performed user-initiated peer review of $y \geq 0$ reported image studies. In this more particular example, the apparatus may be caused to assign the first user $(n/m-x)$ reported image studies, and assign the second user $(n/m-y)$ reported image studies.

In one example, the apparatus may be caused to identify a target number, identify a plurality of users and assign the target number of reported image studies to the plurality of users for each of a plurality of periods. For each period, then, the apparatus may be caused to identify a target number that indicates a predetermined percentage or fraction of a total number of the plurality of available reported image studies.

BRIEF DESCRIPTION OF THE DRAWINGS

Figure 1:
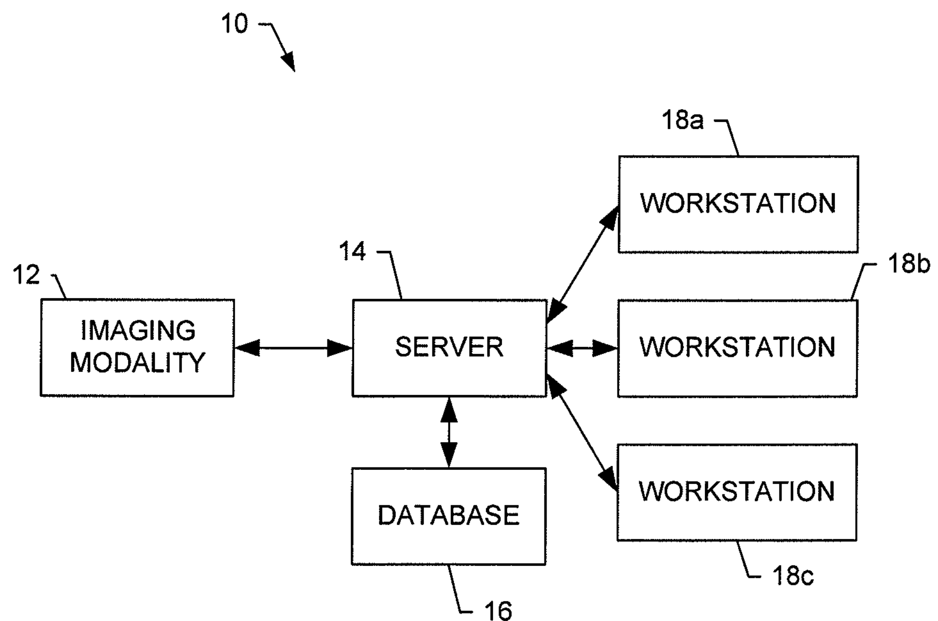
Figure 2:
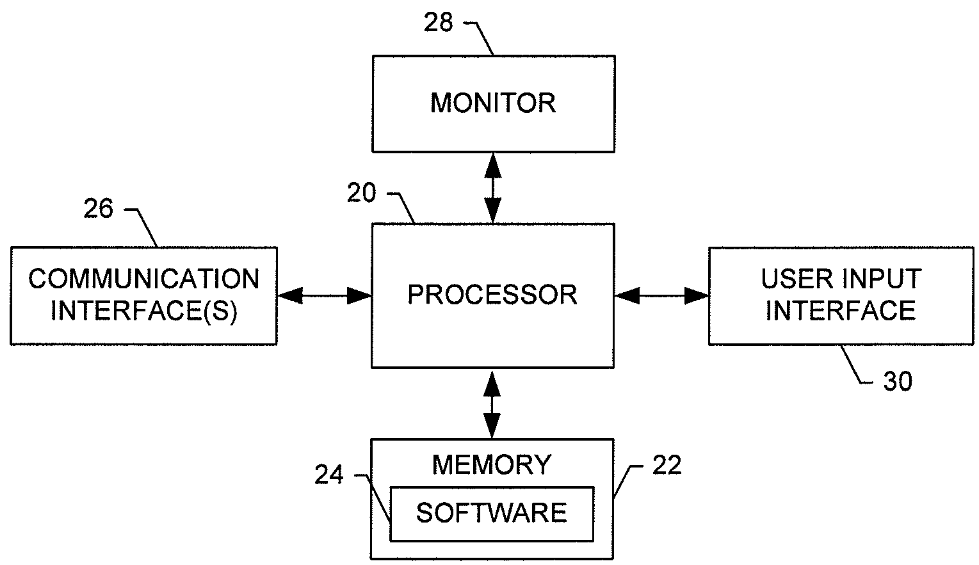
Figure 3:
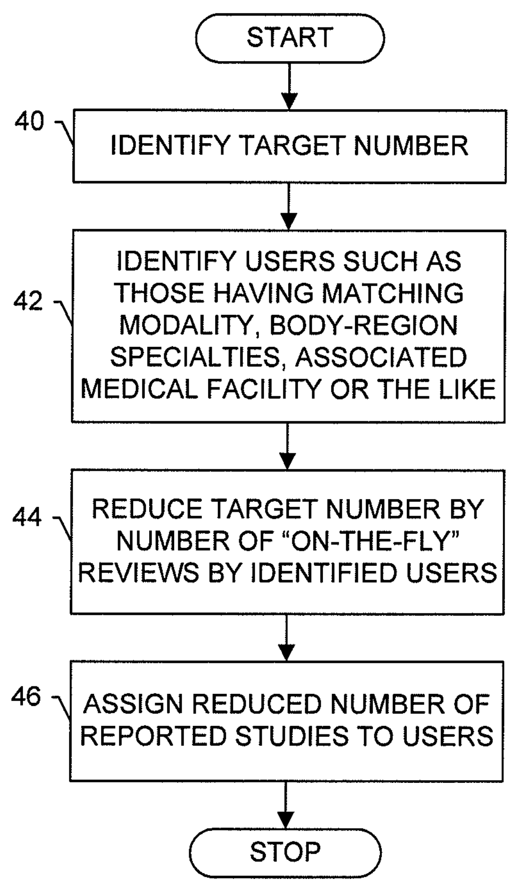

Having thus described the invention in general terms, reference will now be made to the accompanying drawings, which are not necessarily drawn to scale, and wherein:

FIG. 1 is a schematic block diagram of a system configured to operate in accordance with exemplary embodiments of the present invention;

FIG. 2 is a schematic block diagram of an apparatus that may be configured to operate as or otherwise perform one or more functions of one or more of the components of the system of FIG. 1, in accordance with embodiments of the present invention; and FIG. 3 is a flowchart illustrating various operations in a method according to exemplary embodiments of the present invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Further, the apparatus and method of example embodiments of the present invention will be primarily described in conjunction with medical-imaging applications. It should be understood, however, that the apparatus and method can be utilized in conjunction with a variety of other applications, both in the medical industry and outside of the medical industry. Like numbers refer to like elements throughout.

FIG. 1 illustrates a system 10 that may benefit from exemplary embodiments of the present invention ("exemplary" as used herein referring to "serving as an example, instance or illustration"). As shown, the system includes one or more imaging modalities 12 for acquiring an image, such as an image of a region of the human body for clinical purposes such as examination, diagnosis and/or treatment. Examples of suitable modalities include, for example, ultrasound (US), magnetic resonance (MR), positron emission tomography (PET), computed tomography (CT), mammograms (MG) digital radiology (DR), computed radiology (CR) or the like.

The system 10 may also include one or more servers 14 configured to receive image studies from the modalities 12 and other patient information such as patient reports, and archive the images and information in one or more databases 16 or other central storage devices. The server(s) may include any one or more of a database server, image server, web server or the like, which may be separate apparatuses, or which may include an apparatus supporting more than one of the respective servers, logically separated but co-located within the respective apparatus. In one example embodiment, the server (s) and database(s) may form part of one or more of a hospital information system (HIS), radiology information system (RIS), picture archiving and communication system (PACS) or the like. The server(s) may therefore include a HIS server, RIS server, PACS server or the like, each of which is configured to interface with a respective database. In other example embodiments, the server(s) may include a server configured to support multiple ones of a HIS, RIS and/or PACS server, logically separated but co-located within the respective server.

The server 14 may be configured to receive images acquired by the imaging modalities 12, form image studies including the images and archive or otherwise store those image studies in the database 16. Each image study may include one or more acquired images of a patient along with information that may reside with or otherwise accompany the images. This information may include, for example, a study identifer as well as patient information such as the patient's name, demographics, medical record number or the like. The information may also include, for example, an indication of the modality that acquired the images of the study, the body region depicted in the images and/or the medical facility where the modality acquired the images.

The system may further include one or more workstations 18 (three example workstations being shown as workstations 18*a*, 18*b*, 18*c*) by which medical professionals (e.g., radiologists) or other users may access the image studies in the database 16. The server 14 may restrict access to the image studies in the database or may otherwise require medical professionals or other users to login to access the image studies. In such instances, the server may store user profiles for its users. Each user profile may include information regarding a number of characteristics of a user. For example, the user profile may include information such as a user name or other identifier (ID), and/or information identifying one or more specialities of the user, such as a modality specialty, body-region specialty or the like. Additionally or alternatively, for example, the information may identify one or more medical facilities associated with the user, such as facilities employing or otherwise granting privileges to the user.

The workstation 18 may more particularly be configured to receive image studies from the server 14, and present the studies such as for review by a user. The review may include, for example, a medical professional reviewing an unreported study to make one or more diagnoses or other assessments of the patient from the study, which may be recorded in a report. This generated report may then be stored in the database 16, where the report may be linked or otherwise associated with the image study such as by study identifier, patient name, medical record number or the like. An image study that does not yet have an associated report—an associated report has not yet been generated—may be referred to as an unreported study. Conversely, an image study that has an associated report may be referred to as a reported study. In this regard, the workstation may also be configured to receive reported image studies and present the studies such as for peer review by other medical professionals (professionals other than the ones who reported on the studies).

Similar to the server(s) 14, the workstation(s) 18 may be workstation(s) of one or more of a HIS, RIS, PACS or the like. The workstation(s) may therefore include a HIS workstation, RIS workstation, PACS workstation or the like, each of which is configured to interface with a respective server 14 and database 16. In other example embodiments, the workstation (s) may include a workstation configured to support multiple ones of a HIS, RIS and/or PACS workstation, logically separated but co-located within the respective workstation.

The imaging modality 12, server 14, database 16 and/or workstations 18 may be configured to directly and/or indirectly communicate with one another in any of a number of different manners including, for example, any of a number of wireline or wireless communication or networking techniques. Examples of such techniques include, without limitation, Universal Serial Bus (USB), radio frequency (RF), Bluetooth (BT), infrared (IrDA), any of a number of different cellular (wireless) communication techniques such as any of a number of 2G, 2.5G, 3G or 4G communication techniques, local area network (LAN), wireless LAN (WLAN) techniques or the like. In accordance with various ones of these techniques, the imaging modality, server, database and/or workstations may be coupled to and configured to communicate across one or more networks. The network(s) may include any of a number of different combinations of one or more different types of networks, including data and/or voice networks. For example, the network(s) may include one or more data networks, such as a LAN, a metropolitan area network (MAN), and/or a wide area network (WAN) (e.g., Internet), and include one or more voice networks, such as a public-switched telephone network (PSTN). Although not shown, the network(s) may include one or more apparatuses such as one or more routers, switches or the like for relaying data, information or the like between the imaging modality, server, database and/or workstations.

Reference is now made to FIG. 2, which illustrates a block diagram of an apparatus that may be configured to operate as or otherwise perform one or more functions of an imaging modality 12, server 14, database 16 and/or workstation 18. Although shown in FIG. 1 as separate apparatuses, in some embodiments, one or more of the respective apparatuses may support more than one of an imaging modality, server, database and/or workstation, logically separated but co-located within the apparatus(es). For example, a single apparatus may support a logically separate, but co-located server and database; and in the same or another example, a single apparatus may support a logically separate, but co-located server and workstation.

Generally, the apparatus of exemplary embodiments of the present invention may comprise, include or be embodied in one or more fixed electronic devices, such as one or more of a laptop computer, desktop computer, workstation computer, server computer or the like. Additionally or alternatively, the apparatus may comprise, include or be embodied in one or more portable electronic devices, such as one or more of a mobile telephone, portable digital assistant (PDA), pager or the like. The apparatus of exemplary embodiments of the present invention includes various means for performing one or more functions in accordance with exemplary embodiments of the present invention, including those more particularly shown and described herein. It should be understood, however, that one or more of the entities may include alternative means for performing one or more like functions, without departing from the spirit and scope of the present invention.

As shown in FIG. 2, the apparatus may include a processor 20 connected to a memory 22. The memory may include volatile and/or non-volatile memory, and typically stores content, data or the like. In this regard, the memory may store one or more software applications 24, modules, instructions or the like for the processor to perform steps associated with operation of the apparatus in accordance with embodiments of the present invention. The memory may also store content transmitted from, and/or received by, the apparatus. As described herein, the software application(s) may each comprise software operated by the apparatus. It should be understood, however, that any one or more of the software applications described herein may alternatively be implemented by firmware, hardware or any combination of software, firmware and/or hardware, without departing from the spirit and scope of the present invention.

In addition to the memory 22, the processor 20 may also be connected to at least one interface or other means for displaying, transmitting and/or receiving data, content or the like, such as in accordance with USB, RF, BT, IrDA, WLAN, LAN, MAN, WAN (e.g., Internet), PSTN techniques or the like. In this regard, the interface(s) may include at least one communication interface 26 or other means for transmitting and/or receiving data, content or the like. In addition to the communication interface(s), the interface(s) may also include at least one user interface that may include one or more earphones and/or speakers, a monitor 28, and/or a user input interface 30. The user input interface, in turn, can include any of a number of devices allowing the apparatus to receive data from a user, such as a microphone, a keypad, a touch-sensitive surface (integral or separate from the monitor), a joystick, or other input device.

Returning to FIG. 1, as indicated above, the workstation 18 may be configured to receive reported image studies (image studies and associated reports) and present the reported studies such as for peer review by other medical professionals (professionals other than the ones who reported on the studies). A reported study may be peer reviewed by a medical professional (user) in response to a user-initiated request to peer review the reported study. This type of peer review, which may be referred to as an "on the fly," may be initiated by the user in a number of different contexts, such as during the source of the user's normal workflow. For example, a user may perform an on-the-fly peer review in the course of interpreting an unreported study or preparing a teaching file.

In other instances, a reported study may be peer reviewed by a medical professional in response to an assignment of the study to the medical professional. In this regard, the server 14 may at one or more instances (e.g., periodically) assign a plurality of reported studies stored in the database 16 to a plurality of medical professionals for peer review. Example embodiments of the present invention provide techniques for assigning reported studies to medical professionals or other users, which in various examples may be performed by the server although some or all of the techniques may be implemented at other apparatuses including the workstation 18.

Reference is now made to FIG. 3, which illustrates various operations in a method of assigning reported image studies to users according to example embodiments of the present invention. The operations of the method may be performed at one or more instances, or in one example, may be performed periodically for a number of configurable reporting periods (e.g., seven days). During at least some of the reporting periods, one or more reports may have been completed for respective unreported studies, and/or one or more reported studies may have been peer reviewed.

The operations of the method may be further performed on a modality basis, although the description of the operations may be more general to the reported image studies. For example, for reported studies including image studies of a number of different modalities 12, the operations of the method may be performed to separately assign the reported studies for each modality. More particularly, for example, the operations may be performed to separately assign US studies to a plurality of users, assign CT studies to a plurality of users, assign MR studies to a plurality of users, and so forth.

As shown in block 40, the method may include identifying a target number that indicates a number of reported image studies for peer review. The target number may be identified in a number of different manners. In one exemplary embodiment, the target number may be a predetermined percentage or fraction of a total number of reported image studies available for peer review during the reporting period. These available image studies may include those that have not already been peer reviewed or assigned for peer review, and/or those that were reported within a configurable period of time (e.g., six months) of the reporting period.

Consider, for example, an instance in which 1400 reported studies are available for peer review during a reporting period, and the predetermined percentage has been set a 5%. The target number in this example may be identified as 70. In another example in which studies are assigned on a modality basis, consider an instance in which 1200 US, 200 CT and 100 MR reported studies are available during a reporting period, and predetermined percentages have been set respectively at 5%, 3% and 2%. In this other example, target numbers may be identified respectively as 60, 6 and 2.

As shown in block 42, before, after or as the target number is identified, a plurality of users may be identified. The users may be identified in a number of different manners. In one example, the users may be identified based on a comparison of user profiles and information from the reported image studies, such as to identify a plurality of users having user characteristics that match properties of the reported image studies. More particularly, for example, the users may be identified as those who have a modality specialty that matches a modality of the image studies, a body-region specialty that matches a body region of which the image studies include at least one image, and/or an associated medical facility that matches an associated medical facility of the image studies.

In accordance with example embodiments of the present invention, a portion of the identified users may have previously performed an on-the-fly peer review (i.e., a user-initiated peer review) of a number (first number) of reported image studies during the reporting period. In such instances, the target number may be reduced by the number of on-the-fly peer reviews that have been performed, as shown in block 44. The reduced target number of reported studies from the available reported studies may then be assigned to the plurality of users, as shown in block 46. In one example, the reported studies may be randomly or pseudo-randomly assigned to the users. Similarly, the reduced number of reported studies in one example may be randomly or pseudo-randomly selected from the available reported image studies.

In one example, a target number $n \geq 2$ may be identified. In this example, also consider that $m \geq 2$ users may be identified, where at least a portion of the users have previously performed user-initiated peer review of $r \geq 1$ reported image studies. In accordance with exemplary embodiments of the present invention, $(n-r)$ reported image studies may be assigned to the users, where each user may be assigned $n/m$ reported image studies less any of the r reported image studies of which the user has previously performed user-initiated peer review. More particularly, for example, consider the users as including at least a first user having previously performed user-initiated peer review of $x \geq 0$ reported image studies, and a second user having previously performed user-initiated peer review of $y \geq 0$ reported image studies. Even further, consider a third user having previously performed user-initiated peer review of $z \geq 0$ reported image studies. The first user may be assigned $(n/m-x)$ reported image studies, the second user may be assigned $(n/m-y)$ reported image studies, and the third user may be assigned $(n/m-z)$ reported image studies.

In an even more particular example, consider an instance in which a target number of 60 US studies has been identified ($n=60$). In this instance, three users A, B and C have been identified ($m=3$), in which the users have previously performed user-initiated peer review of 8 studies ($r=8$) broken down as follows: A=5 ($x=5$), B=3 ($y=3$) and C=0 ($z=0$). In this example, 52 reported studies ($n-r=60-8=52$) may be assigned to the users as follows: user A may be assigned 15 studies ($(n/m-x)=(60/3-5=15)$, user B may be assigned 17 studies ($(n/m-y)=(60/3-3=17)$, and user C may be assigned 20 studies ($(n/m-x)=(60/3-0=20)$.

As shown and described herein, example embodiments of the present invention account for a number of criteria when assigning reported image studies to identified users. These criteria include, for example, on-the-fly peer reviews that the users have already performed. The criteria also include, for example, modality specialty, body-region specialty, associated medical facility or the like. It should also be understood that any of a number of other criteria may be taken into account when assigning reported image studies. Examples of other criteria may include study status (e.g., only studies marked as reported—as opposed to those including only a preliminary report or dictation—may be peer reviewed), report author (e.g., one may not peer review their own report), study peer review status (e.g., studies that have been peer reviewed or assigned for peer review may not be again assigned) or the like.

According to one aspect of the present invention, all or a portion of the modality 12, server 14, database 16 and/or workstation 18 of exemplary embodiments of the present invention, generally operate under control of a computer program. The computer program for performing the methods of exemplary embodiments of the present invention may include one or more computer-readable program code portions, such as a series of computer instructions, embodied or otherwise stored in a computer-readable storage medium, such as the non-volatile storage medium.

FIG. 3 is a flowchart reflecting methods, systems and computer programs according to exemplary embodiments of the present invention. It will be understood that each block or step of the flowchart, and combinations of blocks in the flowchart, may be implemented by various means, such as hardware, firmware, and/or software including one or more computer program instructions. As will be appreciated, any such computer program instructions may be loaded onto a computer or other programmable apparatus to produce a machine, such that the instructions which execute on the computer or other programmable apparatus (e.g., hardware) create means for implementing the functions specified in the block(s) or step (s) of the flowchart. These computer program instructions may also be stored in a computer-readable memory that may direct a computer or other programmable apparatus to function in a particular manner, such that the instructions stored in the computer-readable memory produce an article of manufacture including instruction means which implement the function specified in the block(s) or step(s) of the flowchart. The computer program instructions may also be loaded onto a computer or other programmable apparatus to cause a series of operational steps to be performed on the computer or other programmable apparatus to produce a computer-implemented process such that the instructions which execute on the computer or other programmable apparatus provide steps for implementing the functions specified in the block(s) or step(s) of the flowchart.

Accordingly, blocks or steps of the flowchart support combinations of means for performing the specified functions, combinations of steps for performing the specified functions and program instructions for performing the specified functions. It will also be understood that one or more blocks or steps of the flowchart, and combinations of blocks or steps in the flowchart, may be implemented by special purpose hardware-based computer systems which perform the specified functions or steps, or combinations of special purpose hardware and computer instructions.

Many modifications and other embodiments of the invention will come to mind to one skilled in the art to which this invention pertains having the benefit of the teachings presented in the foregoing descriptions and the associated drawings. It should therefore be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An apparatus comprising a processor and a memory storing executable instructions that in response to execution by the processor cause the apparatus to at least:

identify a target number that indicates a number of reported image studies for peer review, each reported image study being an image study having an associated report provided by a medical professional;

identify a plurality of users, other than the medical professional who provided the report for a respective reported image study, having user characteristics that match properties of the reported image studies, the user characteristics including at least one of:

a specialty that matches the reported image studies, the specialty including a modality specialty that matches a modality of the reported image studies, and a body-region specialty that matches a body region of which the reported image studies include at least one image; and an associated medical facility that matches an associated medical facility of the reported image studies; and assign the target number of reported image studies from a plurality of available reported image studies to the plurality of users who were identified, the respective plurality of available reported image studies including image studies not having previously been peer reviewed, wherein the apparatus is caused to identify a target number, identify a plurality of users and assign the target number of reported image studies to the plurality of users for each of a plurality of periods, and wherein for each period, the apparatus being caused to identify a target number includes being caused to identify a target number that indicates a predetermined percentage or fraction of a total number of the plurality of available reported image studies.

2. The apparatus of claim 1, wherein the apparatus being caused to identify a plurality of users includes being caused to identify a plurality of users at least a portion of which have previously performed a user-initiated peer review of a first number of reported image studies, wherein the memory stores further executable instructions that in response to execution by the processor cause the apparatus to further reduce the target number by the first number, and wherein the apparatus being caused to assign the target number of reported image studies includes being caused to assign the reduced target number of reported image studies, each user being assigned an equal portion of the target number of reported image studies less any of the first number of reported image studies of which the user has previously performed user-initiated peer review.

3. An apparatus comprising a processor and a memory storing executable instructions that in response to execution by the processor cause the apparatus to at least:

identify a target number that indicates a number of reported image studies for peer review, each reported image study being an image study having an associated report provided by a medical professional, wherein the apparatus being caused to identify a target number includes being caused to identify a target number $n \geq 2$;

identify a plurality of users, other than the medical professional who provided the report for a respective reported image study, having user characteristics that match properties of the reported image studies, the user characteristics including at least one of:

a specialty that matches the reported image studies, the specialty including a modality specialty that matches a modality of the reported image studies, and a body-region specialty that matches a body region of which the reported image studies include at least one image; and an associated medical facility that matches an associated medical facility of the reported image studies, wherein the apparatus being caused to identify a plurality of users includes being caused to identify a plurality of users at least a portion of which have previously performed a user-initiated peer review of a first number of reported image studies, wherein the apparatus being caused to identify a plurality of users includes being caused to identify $m \geq 2$ users, at least a portion of the users having previously performed user-initiated peer review of $r \geq 1$ reported image studies, reduce the target number by the first number;

assign the target number of reported image studies from a plurality of available reported image studies to the plurality of users who were identified, the respective plurality of available reported image studies including image studies not having previously been peer reviewed; and wherein the apparatus being caused to assign the target number of reported image studies includes being caused to assign the reduced target number of reported image studies, each user being assigned an equal portion of the target number of reported image studies less any of the first number of reported image studies of which the user has previously performed user-initiated peer review, and wherein the apparatus being caused to assign the reduced target number of reported image studies includes being caused to assign $(n-r)$ reported image studies, each user being assigned $n/m$ reported image studies less any of the $r$ reported image studies of which the user has previously performed user-initiated peer review.

4. The apparatus of claim 3, wherein the plurality of users includes at least a first user having previously performed user-initiated peer review of $x \geq 0$ reported image studies, and a second user having previously performed user-initiated peer review of $y \geq 0$ reported image studies, and wherein the apparatus being caused to assign the reduced target number of reported image studies includes being caused to assign the first user $(n/m-x)$ reported image studies, and assign the second user $(n/m-y)$ reported image studies.

5. The apparatus of claim 3, wherein the apparatus is caused to identify a target number, identify a plurality of users and assign the target number of reported image studies to the plurality of users for each of a plurality of periods, and wherein for each period, the apparatus being caused to identify a target number includes being caused to identify a target number that indicates a predetermined percentage or fraction of a total number of the plurality of available reported image studies.

6. The apparatus of claim 1, wherein the apparatus being caused to assign the target number of reported image studies includes being caused to assign the target number of reported image studies randomly or pseudo-randomly selected from the plurality of available reported image studies.

7. A method comprising:

identifying a target number that indicates a number of reported image studies for peer review, each reported image study being an image study having an associated report provided by a medical professional;

identifying a plurality of users, other than the medical professional who provided the report for a respective reported image study, having user characteristics that match properties of the reported image studies, the user characteristics including at least one of:

a specialty that matches the reported image studies, the specialty including a modality specialty that matches a modality of the reported image studies, and a body-region specialty that matches a body region of which the reported image studies include at least one image; and an associated medical facility that matches an associated medical facility of the reported image studies; and assigning the target number of reported image studies from a plurality of available reported image studies to the plurality of users, the respective plurality of available reported image studies including image studies not having previously been peer reviewed, wherein identifying a target number, identifying a plurality of and assigning the target number of reported image studies to the plurality of users occur for each of a plurality of periods, wherein for each period, identifying a target number includes identifying a number that indicates a predetermined percentage or fraction of a total number of the plurality of available reported image studies, and wherein identifying a target number, identifying a plurality of users and assigning the target number of reported image studies to the plurality of users who were identified are performed by an apparatus including a processor and a memory storing executable instructions that in response to execution by the processor cause the apparatus to at least identify the target number, identify the plurality of users and assign the target number of reported image studies.

8. The method of claim 7, wherein identifying a plurality of users includes identifying a plurality of users at least a portion of which have previously performed a user-initiated peer review of a first number of reported image studies, wherein the method further comprises reducing the target number by the first number, and wherein assigning the target number of reported image studies includes assigning the reduced target number of reported image studies, each user being assigned an equal portion of the target number of reported image studies less any of the first number of reported image studies of which the user has previously performed user-initiated peer review.

9. A method comprising:

identifying a target number that indicates a number of reported image studies for peer review, each reported image study being an image study having an associated report provided by a medical professional, wherein identifying a target number includes identifying a target number $n \geq 2$;

identifying a plurality of users, other than the medical professional who provided the report for a respective reported image study, having user characteristics that match properties of the reported image studies, the user characteristics including at least one of:

a specialty that matches the reported image studies, the specialty including a modality specialty that matches a modality of the reported image studies, and a body-region specialty that matches a body region of which the reported image studies include at least one image; and an associated medical facility that matches an associated medical facility of the reported image studies, wherein identifying a plurality of users includes identifying a plurality of users at least a portion of which have previously performed a user-initiated peer review of a first number of reported image studies, and wherein identifying a plurality of users includes identifying $m \geq 2$ users, at least a portion of the users having previously performed user-initiated peer review of $r \geq 1$ reported image studies, reducing the target number by the first number; and assigning the target number of reported image studies from a plurality of available reported image studies to the plurality of users, the respective plurality of available reported image studies including image studies not having previously been peer reviewed, wherein assigning the target number of reported image studies includes assigning the reduced target number of reported image studies, each user being assigned an equal portion of the target number of reported image studies less any of the first number of reported image studies of which the user has previously performed user-initiated peer review, and wherein assigning the reduced target number of reported image studies includes assigning $(n-r)$ reported image studies, each user being assigned $n/m$ reported image studies less any of the r reported image studies of which the user has previously performed user-initiated peer review, wherein identifying a target number, identifying a plurality of users and assigning the target number of reported image studies to the plurality of users who were identified are performed by an apparatus including a processor and a memory storing executable instructions that in response to execution by the processor cause the apparatus to at least identify the target number, identify the plurality of users and assign the target number of reported image studies.

10. The method of claim 9, wherein the plurality of users includes at least a first user having previously performed user-initiated peer review of $x \geq 0$ reported image studies, and a second user having previously performed user-initiated peer review of $y \geq 0$ reported image studies, and wherein assigning the reduced target number of reported image studies includes assigning the first user $(n/m-x)$ reported image studies, and assigning the second user $(n/m-y)$ reported image studies.

11. The method of claim 9, wherein identifying a target number, identifying a plurality of and assigning the target number of reported image studies to the plurality of users occur for each of a plurality of periods, and wherein for each period, identifying a target number includes identifying a number that indicates a predetermined percentage or fraction of a total number of the plurality of available reported image studies.

12. The method of claim 7, wherein assigning the target number of reported image studies includes assigning the target number of reported image studies randomly or pseudo-randomly selected from the plurality of available reported image studies.

13. A computer-readable storage medium having computer-readable program code portions stored therein that in response to execution by a processor cause an apparatus to at least:

identify a target number that indicates a number of reported image studies for peer review, each reported image study being an image study having an associated report provided by a medical professional;

identify a plurality of users, other than the medical professional who provided the report for a respective reported image study, having user characteristics that match properties of the reported image studies, the user characteristics including at least one of:

a specialty that matches the reported image studies, the specialty including a modality specialty that matches a modality of the reported image studies, and a body-region specialty that matches a body region of which the reported image studies include at least one image; and an associated medical facility that matches an associated medical facility of the reported image studies; and assign the target number of reported image studies from a plurality of available reported image studies to the plurality of users who were identified, the respective plurality of available reported image studies including image studies not having previously been peer reviewed, wherein the apparatus is caused to identify a target number, identify a plurality of users and assign the target number of reported image studies to the plurality of users for each of a plurality of periods, and wherein for each period, the apparatus being caused to identify a target number includes being caused to identify a target number that indicates a predetermined percentage or fraction of a total number of the plurality of available reported image studies.

14. The computer-readable storage medium of claim 13, wherein the apparatus being caused to identify a plurality of users includes being caused to identify a plurality of users at least a portion of which have previously performed a user-initiated peer review of a first number of reported image studies, wherein the computer-readable storage medium has further computer-readable program code portions stored therein that in response to execution by the processor cause the apparatus to further reduce the target number by the first number, and wherein the apparatus being caused to assign the target number of reported image studies includes being caused to assign the reduced target number of reported image studies, each user being assigned an equal portion of the target number of reported image studies less any of the first number of reported image studies of which the user has previously performed user-initiated peer review.

15. A computer-readable storage medium, having computer-readable program code portions stored therein that in response to execution by a processor cause an apparatus to at least:

identify a target number that indicates a number of reported image studies for peer review, each reported image study being an image study having an associated report provided by a medical professional, wherein the apparatus being caused to identify a target number includes being caused to identify a target number $n \geq 2$, identify a plurality of users, other than the medical professional who provided the report for a respective reported image study, having user characteristics that match properties of the reported image studies, the user characteristics including at least one of:

a specialty that matches the reported image studies, the specialty including a modality specialty that matches a modality of the reported image studies, and a body-region specialty that matches a body region of which the reported image studies include at least one image; and an associated medical facility that matches an associated medical facility of the reported image studies, wherein the apparatus being caused to identify a plurality of users includes being caused to identify a plurality of users at least a portion of which have previously performed a user-initiated peer review of a first number of reported image studies, and wherein the apparatus being caused to identify a plurality of users includes being caused to identify $m \geq 2$ users, at least a portion of the users having previously performed user-initiated peer review of $r \geq 1$ reported image studies;

reduce the target number by the first number; and assign the target number of reported image studies from a plurality of available reported image studies to the plurality of users who were identified, the respective plurality of available reported image studies including image studies not having previously been peer reviewed, wherein the apparatus being caused to assign the target number of reported image studies includes being caused to assign the reduced target number of reported image studies, each user being assigned an equal portion of the target number of reported image studies less any of the first number of reported image studies of which the user has previously performed user-initiated peer review, and wherein the apparatus being caused to assign the reduced target number of reported image studies includes being caused to assign $(n-r)$ reported image studies, each user being assigned $n/m$ reported image studies less any of the r reported image studies of which the user has previously performed user-initiated peer review.

16. The computer-readable storage medium of claim 15, wherein the plurality of users includes at least a first user having previously performed user-initiated peer review of $x \geq 0$ reported image studies, and a second user having previously performed user-initiated peer review of $y \geq 0$ reported image studies, and wherein the apparatus being caused to assign the reduced target number of reported image studies includes being caused to assign the first user $(n/m-x)$ reported image studies, and assign the second user $(n/m-y)$ reported image studies.

17. The computer-readable storage medium of claim 15, wherein the apparatus is caused to identify a target number, identify a plurality of users and assign the target number of reported image studies to the plurality of users for each of a plurality of periods, and wherein for each period, the apparatus being caused to identify a target number includes being caused to identify a target number that indicates a predetermined percentage or fraction of a total number of the plurality of available reported image studies.

18. The computer-readable storage medium of claim 13, wherein the apparatus being caused to assign the target number of reported image studies includes being caused to assign the target number of reported image studies randomly or pseudo-randomly selected from the plurality of available reported image studies.

* * * * *